US00PP18196P2

(12) United States Plant Patent
Verschoor

(10) Patent No.: US PP18,196 P2
(45) Date of Patent: Nov. 13, 2007

(54) ***PHLOX* PLANT NAMED 'PEPPERMINT TWIST'**

(50) Latin Name: *Phlox paniculata*
Varietal Denomination: Peppermint Twist

(75) Inventor: Jan Verschoor, Haarlem (NL)

(73) Assignee: Witteman + Co., Hillegom (NL)

( * ) Notice: Subject to any disclaimer, the term of this patent is extended or adjusted under 35 U.S.C. 154(b) by 0 days.

(21) Appl. No.: 11/454,069

(22) Filed: Jun. 15, 2006

(51) Int. Cl.
*A01H 5/00* (2006.01)

(52) U.S. Cl. ..... Plt./320

(58) Field of Classification Search ..... Plt./320
See application file for complete search history.

*Primary Examiner*—Kent Bell
(74) *Attorney, Agent, or Firm*—C. A. Whealy

(57) ABSTRACT

A new and distinct cultivar of *Phlox* plant named 'Peppermint Twist', characterized by its upright and compact plant habit; freely basally branching habit and relatively short internodes; dense and bushy growth habit; attractive red purple and white bi-colored flowers; freely and continuous flowering habit; resistance to Powdery Mildew; and good garden performance.

2 Drawing Sheets

Botanical designation: *Phlox paniculata.*
Cultivar denomination: 'Peppermint Twist'.

REFERENCED APPLICATIONS

*Phlox* Plant Named 'Candy Floss'; Jan Verschoor, applicant; filed concurrently (U.S. Plant patent application Ser. No. 11/454,068).

BACKGROUND OF THE INVENTION

The present invention relates to a new and distinct cultivar of *Phlox,* botanically known as *Phlox paniculata* and hereinafter referred to by the name 'Peppermint Twist'.

The new *Phlox* is a naturally-occurring branch mutation of the *Phlox paniculata* cultivar 'Candy Floss', disclosed in U.S. Plant patent application Ser. No. 11/454,068. The new *Phlox* was discovered and selected by the Inventor in a controlled environment in Haarlem, The Netherlands in 2001.

Asexual reproduction of the new *Phlox* by vegetative cuttings in a controlled environment in Haarlem, The Netherlands since August, 2001, has shown that the unique features of this new *Phlox* are stable and reproduced true to type in successive generations.

SUMMARY OF THE INVENTION

The cultivar Peppermint Twist has not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Peppermint Twist'. These characteristics in combination distinguish 'Peppermint Twist' as a new and distinct cultivar of *Phlox:*

1. Upright and compact plant habit.
2. Freely basally branching habit; dense and bushy growth habit.

3. Attractive red purple and white bi-colored flowers.
4. Freely and continuous flowering habit.
5. Resistant to Powdery Mildew.
6. Good garden performance.

Plants of the new *Phlox* and the parent, the cultivar 'Candy Floss', differ primarily in flower coloration.

Plants of the new *Phlox* can also be compared to plants of the cultivar Little Princess, disclosed in U.S. Plant Pat. No. 13,742. In side-by-side comparisons conducted in Haarlem, The Netherlands, plants of the new *Phlox* and the cultivar Little Princess differed primarily in flower color as plants of the cultivar Little Princess had pink-colored flowers. In addition, plants of the new *Phlox* were more resistant to Powdery Mildew than plants of the cultivar Little Princess.

BRIEF DESCRIPTION OF THE PHOTOGRAPHS

The accompanying colored photographs illustrate the overall appearance of the new *Phlox,* showing the colors as true as it is reasonably possible to obtain in colored reproductions of this type. Colors in the photographs may differ slightly from the color values cited in the detailed botanical description which accurately describe the colors of the new *Phlox.*

The photograph on the first sheet comprises a side perspective view of a typical flowering plant of 'Peppermint Twist' grown in an outdoor nursery.

The photograph on the second sheet is a close-up view of a typical inflorescence of 'Peppermint Twist'.

DETAILED BOTANICAL DESCRIPTION

The aforementioned photographs and following observations, measurements and values describe plants grown in Haarlem, The Netherlands, under commercial practice during the summer in an outdoor nursery with day temperatures ranging from 18° C. to 32° C. and night temperatures ranging from 10° C. to 18° C. Plants were grown for about one year when the photograph and description were taken. In the following description, color references are made to The Royal Horticultural Society Colour Chart, 2001 Edition, except where general terms of ordinary dictionary significance are used.

Botanical classification: *Phlox paniculata* cultivar 'Peppermint Twist'.

Parentage: Naturally-occurring branch mutation of the *Phlox paniculata* cultivar 'Candy Floss', disclosed in U.S. Plant patent application Ser. No. 11/454,068.

Propagation:

*Type.*—By vegetative cuttings.

*Time to produce a rooted plant.*—About four weeks.

*Root description.*—Fine; white in color.

Plant description:

*Plant form/habit.*—Upright and compact plant habit; inverted triangle; moderately vigorous growth habit. Freely basally branching habit; dense and bushy growth habit.

*Plant height.*—About 41 cm.

*Plant width (spread).*—About 33 cm.

*Lateral branches.*—Length: About 23.2 cm. Diameter: About 5 mm. Internode length: About 2.4 cm. Strength: Strong. Texture: Smooth, glabrous. Color: 144B.

Foliage description:

*Arrangement.*—Opposite, simple.

*Length.*—About 8.7 cm.

*Width.*—About 3 cm.

*Shape.*—Elliptic.

*Apex.*—Apiculate.

*Base.*—Attenuate.

*Margin.*—Finely serrate.

*Texture, upper and lower surfaces.*—Smooth, glabrous.

*Venation pattern.*—Pinnate.

*Color.*—Developing leaves, upper surface: 143A. Developing leaves, lower surface: 143B to 143C. Fully expanded leaves, upper surface: Slightly darker than 139A; venation, 144B to 144C. Fully expanded leaves, lower surface: 137B to 137C; venation, 144B to 144C.

*Petiole.*—Length: About 2 mm. Diameter: About 4 mm. Texture, upper and lower surfaces: Smooth, glabrous. Color, upper and lower surfaces: 144A to 144B.

Flower description:

*Flower type/habit.*—Single rotate and salverform flowers arranged in terminal panicles; flowers face upright and outward. Panicles conical in shape. Freely flowering habit with about 150 flower buds and flowers per inflorescence.

*Fragrance.*—Fragrant; sweet.

*Natural flowering season.*—Continuously flowering from July through August in Haarlem, The Netherlands. Flowers not persistent.

*Postproduction longevity.*—Flowers last about ten days on the plant.

*Flower buds.*—Height: About 1.5 cm. Diameter: About 4.5 mm. Shape: Elliptic. Color: 155C; towards the apex, 68D.

*Inflorescence height.*—About 17.8 cm.

*Inflorescence diameter.*—About 18.1 cm.

*Flower diameter.*—About 3.6 cm.

*Flower depth.*—About 2.9 cm.

*Petals.*—Quantity per flower: Typically five in a single whorl; petals fused at the base into a narrow tube. Length: About 3.4 cm. Lobe width: About 1.8 cm. Shape: Spatulate. Apex: Retuse. Margin: Entire. Texture, upper and lower surfaces: Smooth, glabrous. Color: Developing and fully expanded petals, upper surface: 58B to 58C; towards the margins, 155C, about 4 mm in width; throat, N77B. With development, color becoming closer to 62A; towards the margins, 155C, about 4 mm in width; throat, N77B. Developing and fully expanded petals, lower surface: 62A; towards the margins, 155C, about 4 mm in width; throat, N77B to N77D.

*Sepals.*—Quantity per flower: Typically five in a single whorl, fused; narrow tubular calyx. Length: About 1 cm. Width: About 1.5 mm. Calyx shape: Campanulate. Apex: Narrowly apiculate. Margin: Entire. Texture, upper and lower surfaces: Smooth, glabrous. Color, developing sepals, upper and lower surfaces: Towards the base, 144B; towards the apex, 146A to 147A. Color, fully expanded sepals, upper and lower surfaces: Towards the base, 144B; towards the apex, 146A to 147A.

*Peduncles.*—Length: About 12.9 cm. Diameter: About 3 mm. Angle: Erect to about 45° from vertical. Strength: Strong. Texture: Smooth, glabrous. Color: 144B.

*Pedicels.*—Length: About 6 mm. Diameter: About 0.75 mm. Angle: About 25° to about 50° from vertical. Strength: Strong. Texture: Smooth, glabrous. Color: 146A to 146B.

*Reproductive organs.*—Stamens: Quantity per flower: Typically five; fused with petals in tube. Filament length: About 2 mm. Anther shape: Oblong. Anther length: About 1 mm. Anther color: 5D. Pollen amount: Scarce. Pollen color: 5D to 6D. Pistils: Quantity per flower: One. Pistil length: About 2.1 cm. Stigma shape: Three-parted. Stigma color: 150D. Style length: About 1.9 cm. Style color: 150C. Ovary color: 143A.

*Seed/fruit.*—Seed and fruit development have not been observed.

Disease/pest resistance: Plants of the new *Phlox* have been noted to be resistant to Powdery Mildew. Plants of the new *Phlox* have not been noted to be resistant to other pathogens and pests common to *Phlox*.

Garden performance: Plants of the new *Phlox* have been observed to have good garden performance and tolerate rain, wind and are winter hardy in The Netherlands.

It is claimed:

1. A new and distinct *Phlox* plant named 'Peppermint Twist' as illustrated and described.

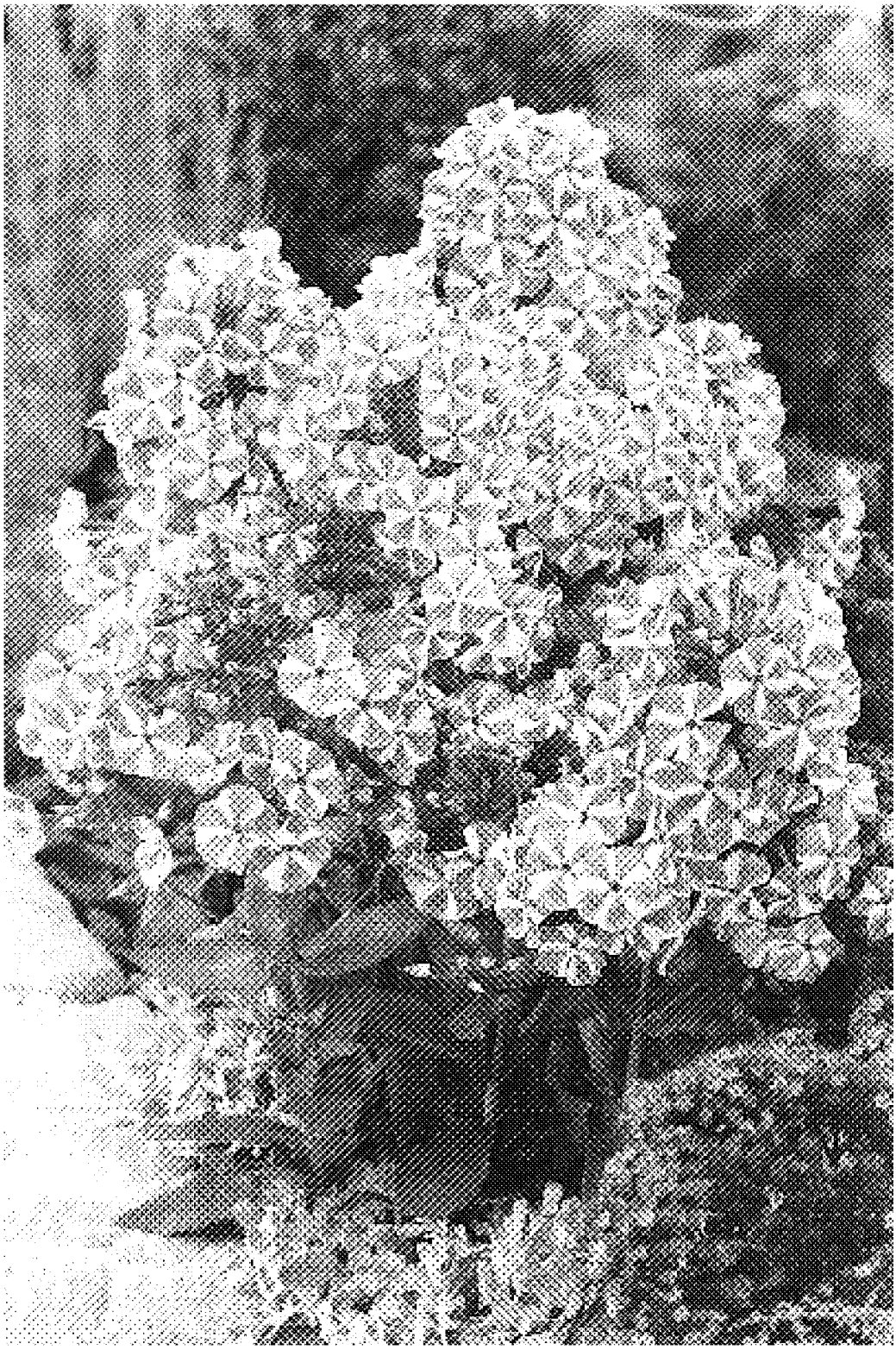

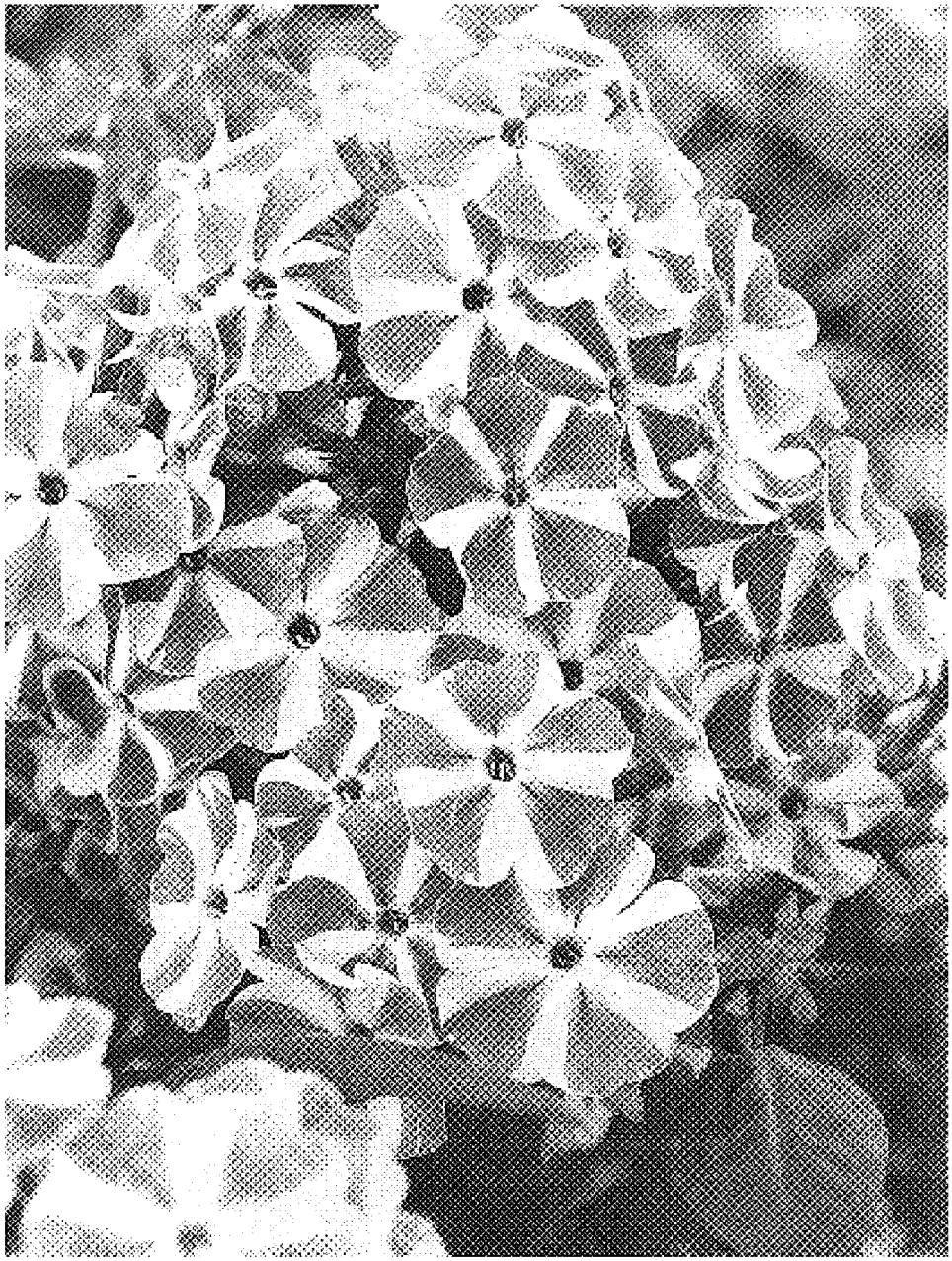

* * * * *